(12) United States Patent
Kim

(10) Patent No.: US 11,654,071 B2
(45) Date of Patent: May 23, 2023

(54) BED FOR ENDOSCOPIC EXAMINATION OF STOMACH AND LARGE INTESTINE

(71) Applicant: Hyunghun Kim, Seoul (KR)

(72) Inventor: Hyunghun Kim, Seoul (KR)

( * ) Notice: Subject to any disclaimer, the term of this patent is extended or adjusted under 35 U.S.C. 154(b) by 92 days.

(21) Appl. No.: 17/392,626

(22) Filed: Aug. 3, 2021

(65) Prior Publication Data

US 2022/0117820 A1 Apr. 21, 2022

(30) Foreign Application Priority Data

Oct. 19, 2020 (KR) .......................... 10-2020-0134955

(51) Int. Cl.
*A61G 13/12* (2006.01)
*A61B 5/00* (2006.01)

(52) U.S. Cl.
CPC ........ *A61G 13/1285* (2013.01); *A61B 5/4255* (2013.01); *A61B 5/704* (2013.01); *A61G 13/123* (2013.01)

(58) Field of Classification Search
CPC .............. A61G 13/1285; A61G 13/123; A61G 13/121; A61G 13/04; A61G 13/08; A61G 13/10; A61G 13/0018; A61G 7/008; A61G 7/05; A61G 2200/32; A61G 2203/70; A61G 2210/00; A61G 13/1245; A61G 13/104; A61G 13/06; A61G 13/129; A61G 13/128; A61B 5/704; A61B 1/00147; A61B 90/57; A61B 2090/571; A61B 1/31; A61B 5/4255
See application file for complete search history.

(56) References Cited

FOREIGN PATENT DOCUMENTS

| CN | 213310687 U | * | 7/2020 | ............. A61F 5/042 |
| JP | H07303653 A | * | 5/1994 | ............. A61B 17/00 |
| JP | 2000-296158 A | | 10/2000 | |
| JP | 2003-204922 A | | 7/2003 | |
| JP | 2003204922 | * | 7/2003 | ............... A61B 1/00 |
| JP | 3133247 U | | 6/2007 | |

* cited by examiner

*Primary Examiner* — David R Hare
*Assistant Examiner* — Madison Emanski
(74) *Attorney, Agent, or Firm* — United One Law Group LLC; Kongsik Kim; Jhongwoo Peck

(57) ABSTRACT

Proposed is a bed for endoscopic examination of the stomach and the large intestine, the bed being configured to enable a distance to a patient to be narrowed in a case of the endoscopic examination of the large intestine and a patient's head to be tilted in a case of the endoscopic examination of the stomach. To this end, the bed may at least include: a central main body configured to support at least a part of the torso and the buttocks of a patient; a lower main body configured to be coupled to the central main body by a pitching shaft at a buttocks side of a patient so that a pitching movement is possible with the central main body as a reference; and a pitching coupling unit configured to allow the lower main body to perform a pitching movement with the central main body as the reference.

4 Claims, 10 Drawing Sheets

BED FOR ENDOSCOPIC EXAMINATION OF STOMACH AND LARGE INTESTINE

CROSS REFERENCE TO RELATED APPLICATION

The present application claims priority to Korean Patent Application No. 10-2020-0134955 filed on Oct. 19, 2020, the entire contents of which are incorporated herein by reference for all purposes.

TECHNICAL FIELD

The present disclosure relates to a bed for endoscopic examination of the stomach and the large intestine, more particularly, to a bed for endoscopic examination of the stomach and the large intestine, the bed being configured to enable a distance to a patient to be narrowed in a case of the endoscopic examination of the large intestine and a patient's head to be tilted in a case of the endoscopic examination of the stomach.

RELATED ART

In general, in the medical field, endoscopic examination is widely performed using an endoscope that is inserted into a patient. In particular, endoscopic examination of the stomach and the large intestine is widely performed. Such endoscopic examination uses an electronic endoscope equipped with an imaging means that may easily record an observation image in real-time.

In the case of the endoscopic examination using the electronic endoscope, an operator inserts the endoscope into a patient while looking at: a trolley loaded with a video processor that processes signals to the imaging means of the electronic endoscope; a light source device that supplies illumination light to the illumination guide of the electronic endoscope; and an observation monitor that displays the observation image.

In upper examinations such as upper digestive tract examination and the like, a direction of insertion of the endoscope coincides with a direction of the operator's body, but in lower examinations, the direction of insertion of the endoscope, which is a longitudinal direction of the bed, does not coincide with the direction of the operator's body. Therefore, it is required for the operator to set the observation monitor at a tip of the bed next to the patient and to have the dexterity of inserting the endoscope while leaning to the bed so as to face the observation monitor.

DOCUMENTS OF RELATED ART

Patent Documents (Patent Document 1) Japanese Patent Application Publication No. 10-2000-296158 (Title: a bed for endoscopic examination, publication date: Oct. 24, 2000)

SUMMARY

Accordingly, the present disclosure has been made keeping in mind the above problems occurring in the related art, and an objective of the present disclosure is to provide a bed for endoscopic examination of the stomach and the large intestine, the bed being configured to enable a distance to a patient to be narrowed in a case of the endoscopic examination of the large intestine and a patient's head to be tilted in a case of the endoscopic examination of the stomach.

In order to achieve the above objective, according to an exemplary embodiment of the present disclosure, there may be provided a bed for endoscopic examination of the stomach and the large intestine, the bed including: a central main body configured to support at least a part of the torso and the buttocks of a patient; a lower main body configured to be coupled to the central main body by a pitching shaft at a buttocks side of the patient so that a pitching movement is possible with the central main body as a reference; and a pitching coupling unit configured to allow the lower main body to perform the pitching movement with the central main body as a reference.

The bed for the endoscopic examination of the stomach and the large intestine according to the present disclosure may further include: an upper main body configured to be coupled to the central main body by a rolling shaft at a head side of the patient so that a rolling movement is possible with the central main body as a reference; and a rolling coupling unit configured to allow the upper main body to perform the rolling movement with the central main body as a reference.

Here, the pitching coupling unit may include at least any one of: a sliding module connected at one side thereof to a support leg provided at a part under the central main body and coupled at an opposite side thereof to the lower main body, thereby being configured to adjust a length thereof in a telescopic method; a ratchet module configured to rotate the pitching shaft forwardly and reversely in a ratchet gear method; and a worm gear module configured to rotate the pitching shaft forwardly and reversely in a worm gear method.

The bed for the endoscopic examination of the stomach and the large intestine according to the present disclosure may further include a mounting module protrudingly formed in the lower main body and configured to support an endoscopic cable when the lower main body is folded with the central main body as a reference.

Here, the mounting module may include: a mounting part provided in the lower main body; a first support ring rotatably coupled to the mounting part with a first shaft as a center; a second support ring rotatably coupled to the mounting part with a second shaft as a center while being spaced apart from the first support ring; and a locking part configured to couple the first support ring and the second support ring to each other when the first support ring and the second support ring wrap the endoscopic cable.

Here, the mounting part may be configured to be detachable from the lower main body, and the mounting module may further include: a longitudinal groove recessively formed in the lower main body; and a lifting rod extending from the mounting part and configured to be slidingly movable in a state of being fittedly coupled in the longitudinal groove.

Here, the mounting part may be configured to be detachable from the lower main body, and the mounting module may further include: a reciprocating guide formed longitudinally in a width direction of the lower main body; and a sliding part provided in the mounting part so as to be slidingly movable in a state of being fittedly coupled with the reciprocating guide.

A bed for endoscopic examination of the stomach and the large intestine according to the present disclosure may further include: a central main body configured to support at least a part of the torso and the buttocks of a patient; an upper main body configured to be coupled to the central main body by a rolling shaft at a head side of the patient so that a rolling movement is possible with the central main body as a reference; and a rolling coupling unit configured to allow the upper main body to perform the rolling movement with the central main body as a reference.

According to the bed for the endoscopic examination of the stomach and the large intestine of the present disclosure, a distance to a patient can be narrowed in a case of the endoscopic examination of the large intestine and a patient's head can be tilted in a case of the endoscopic examination of the stomach.

In addition, in the present disclosure, it is possible to prevent the lower main body from being rotated downward unexpectedly due to an operation method of the pitching coupling unit, so a safety accident can be prevented.

In addition, in the present disclosure, the lower main body can be supported under a bottom part of the bed by a telescopic mechanism of the pitching coupling unit, so it is possible to prevent the lower main body from being rotated downward unexpectedly.

In addition, in the present disclosure, rotation directions can be limited due to the ratchet gear mechanism in the pitching coupling unit, so it is possible to prevent the lower main body from being rotated downward unexpectedly.

In addition, in the present disclosure, an input part and an output part for rotation can be limited due to the worm gear mechanism in the pitching coupling unit, so it is possible to prevent the lower main body from being rotated downward unexpectedly.

In addition, in the present disclosure, it is possible to prevent the upper main body from an unexpected rolling rotation due to an operation of the rolling coupling unit, so a safety accident can be prevented.

In addition, in the present disclosure, an input part and an output part for rotation can be limited due to the worm gear mechanism in the rolling coupling unit, so it is possible to prevent the upper main body from the unexpected rolling rotation to the left and right.

In addition, in the present disclosure, a bevel gear mechanism can be added, so a position for operating the upper main body can be changed.

In addition, in the present disclosure, the endoscopic cable can be fixed to a fixed position by using the mounting module.

In addition, in the present disclosure, due to an efficient configuration of the mounting module, the endoscopic cable can be gripped using tongs, the state of the endoscopic cable being gripped can be stably maintained, and the detachably-coupled state of the first support ring and the second support ring can be stabilized.

In addition, in the present disclosure, the height of the mounting part can be efficiently adjusted by using the lifting structure of the mounting module.

In addition, in the present disclosure, the position of the mounting part can be adjusted with a reference of a width direction of the central main body by using the lifting structure of the mounting module.

In addition, in the present disclosure, manpower required for performing the endoscopic examination can be minimized and thus the cost required therefor can be reduced.

BRIEF DESCRIPTION OF THE DRAWINGS

The above and other objectives, features, and advantages of the present disclosure will be more clearly understood from the following detailed description when taken in conjunction with the accompanying drawings, in which.

DETAILED DESCRIPTION

Figure 1:
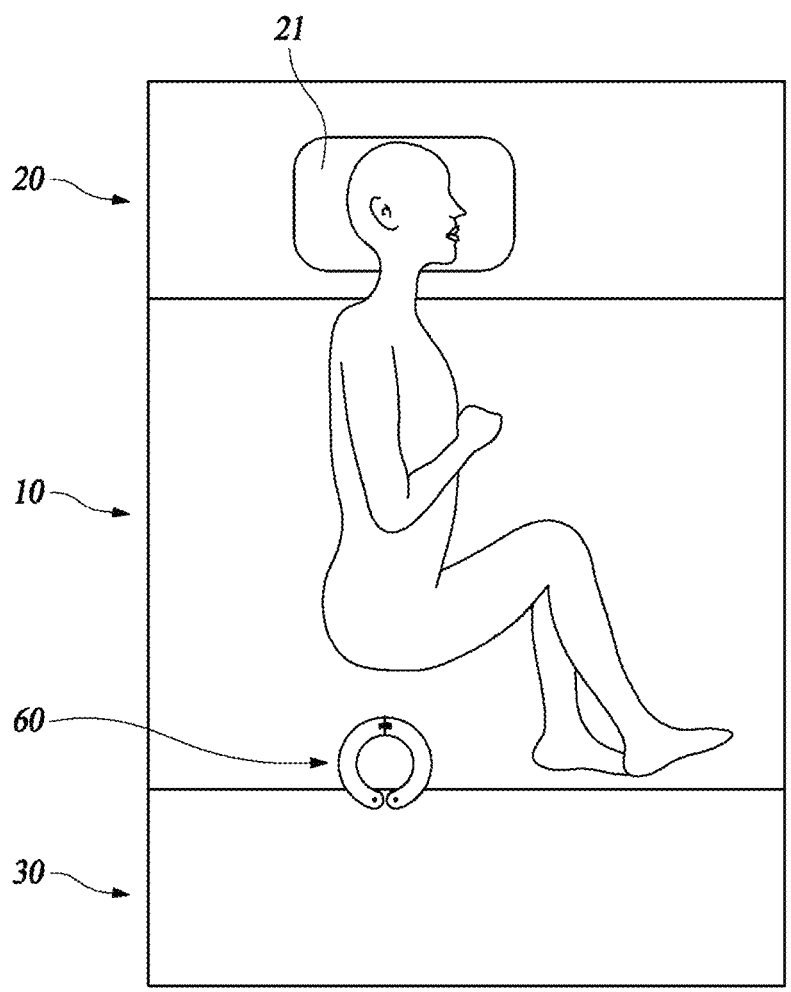
FIG. 1 is a plan view showing a bed for endoscopic examination of the stomach and the large intestine according to an embodiment of the present disclosure.

Hereinafter, with reference to the accompanying drawings, an embodiment of a bed for endoscopic examination of the stomach and the large intestine according to the present disclosure will be described. At this time, the present disclosure is not limited to or limited by the embodiments. In addition, in describing the present disclosure, detailed descriptions of well-known functions or configurations may be omitted in order to clarify the gist of the present disclosure.

The bed for the endoscopic examination of the stomach and the large intestine according to the present disclosure may be used for performing the endoscopic examination of the large intestine as well as the endoscopic examination of the stomach.

The bed for the endoscopic examination of the stomach and the large intestine according to an embodiment of the present disclosure may include: a central main body 10 configured to support at least a part of the torso and the buttocks of a patient; a lower main body 30 configured to be coupled to the central main body 10 by a pitching shaft 12 at a buttocks side of the patient so that a pitching movement is possible with the central main body 10 as a reference; and a pitching coupling unit 40 configured to allow the lower main body 30 to perform a pitching movement with the central main body 10 as the reference.

Here, the pitching coupling unit 40 may include at least any one of: a sliding module 410 connected at one side thereof to a support leg 11 provided at a part under the central main body 10 and coupled at an opposite side thereof to the lower main body 30, thereby being configured to adjust a length thereof in a telescopic method; a ratchet module 420 configured to rotate the pitching shaft 12 forwardly and reversely in a ratchet gear method; and a worm gear module 430 configured to rotate the pitching shaft 12 forwardly and reversely in a worm gear method.

Figure 3A:
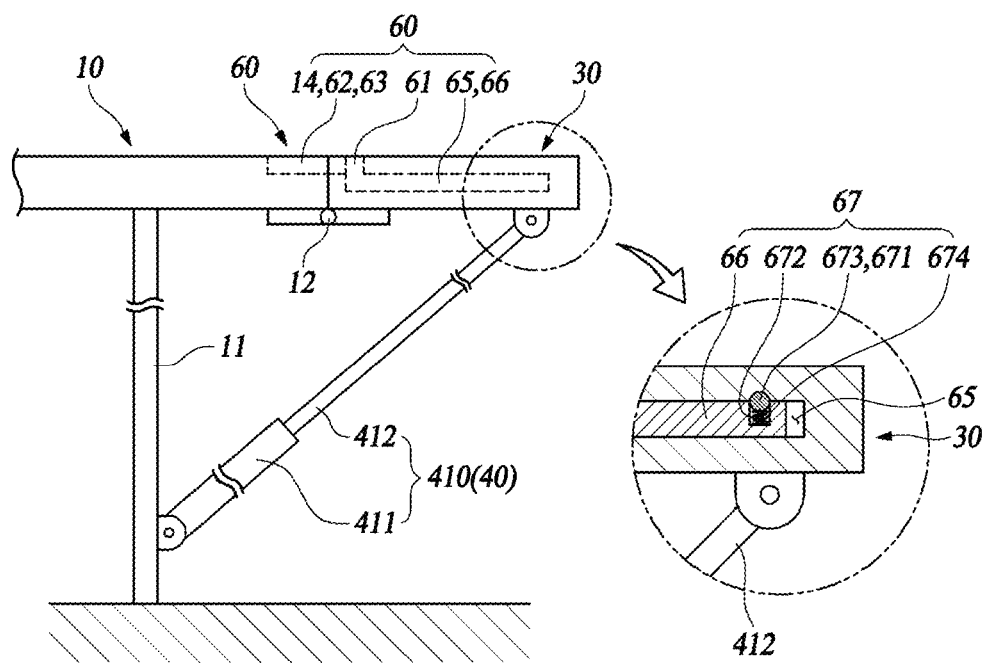
FIGS. 3A and 3B are side views showing operating states of the lower main body, and a first example of a pitching coupling unit in the bed for the endoscopic examination of the stomach and the large intestine according to the embodiment of the present disclosure.
Figure 3B:
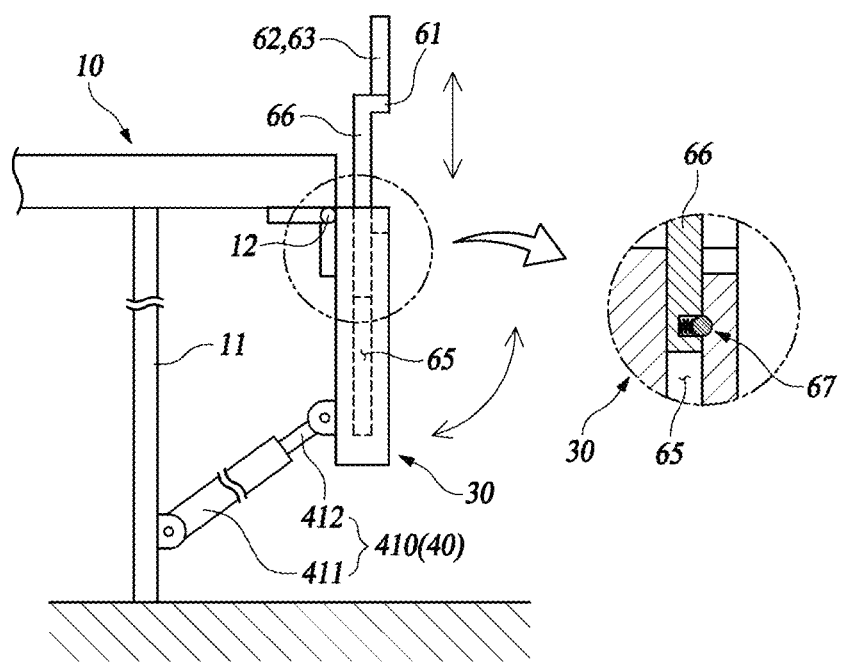
Figure 4:
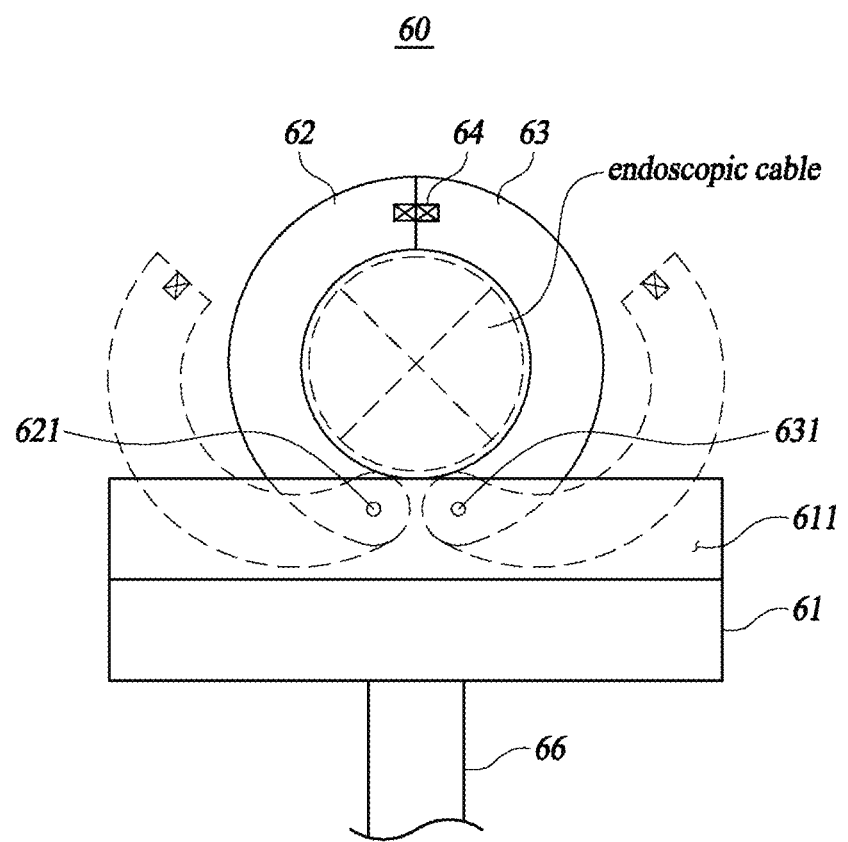
FIG. 4 is a view showing a configuration of a mounting module in the bed for the endoscopic examination of the stomach and the large intestine according to the embodiment of the present disclosure.

First, as shown in FIGS. 3A and 3B, the sliding module 410 may include: a cylinder part 411 rotatably coupled to any one of the support legs 11 and the lower main body 30; and a piston part 412 having one side rotatably coupled to any one of the support legs 11 and lower main body 30 and an opposite side fittedly coupled to the cylinder part 411.

Then, as the cylinder part 411 slidingly moves the piston part 412, the lower main body 30 rotates with the central main body 10 as a reference and the pitching shaft 12 as a center. Here, the sliding module 410 supports a bottom portion of the lower main body 30 below the central main body 10.

Figure 5:
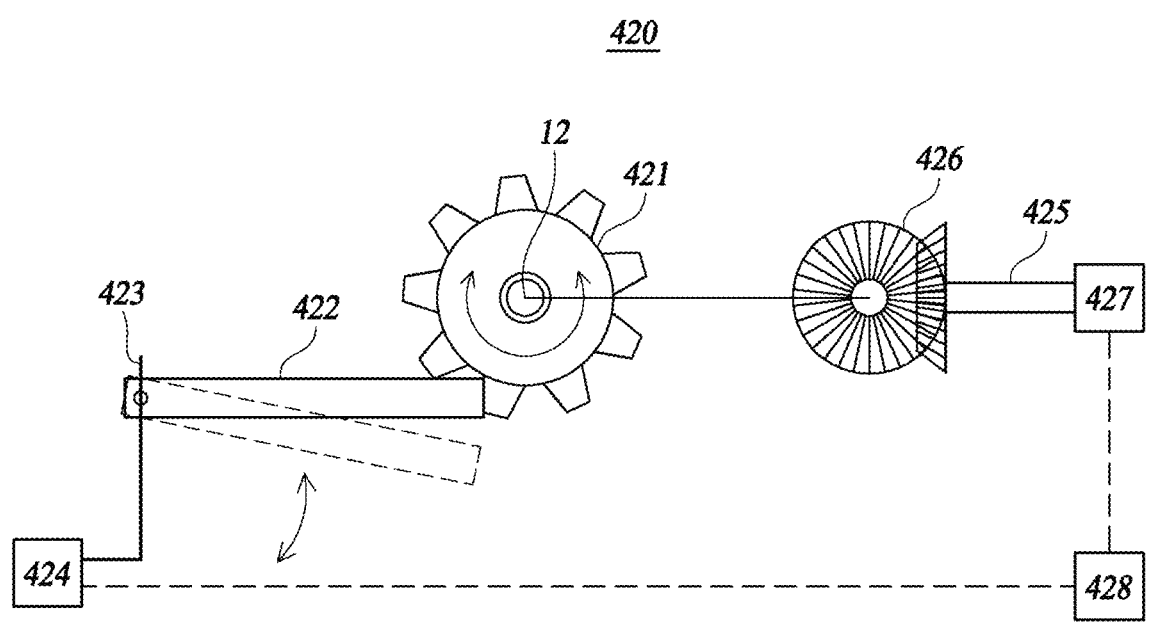
FIG. 5 is a view showing a second example of the pitching coupling unit, which is implemented with a ratchet gear method, in the bed for the endoscopic examination of the stomach and the large intestine according to the embodiment of the present disclosure.

Second, as shown in FIG. 5, the ratchet module 420 may include: a ratchet gear 421 provided on the pitching shaft 12 and configured to rotate together with the pitching shaft 12; a stop member 422 formed longitudinally in a circumferential direction of the ratchet gear 421 and detachably adhered to the ratchet gear 421, a stop elastic member 423 configured to make the stop member 422 elastically press the ratchet gear 421; a stop operation unit 424 configured to make the stop member 422 perform a pivot movement automatically or manually; and a ratchet operation unit 427 configured to rotate the pitching shaft 12 automatically or manually.

Here, the ratchet module 420 may further include a ratchet controller 428 configured to control an operation of the ratchet operation unit 427 according to an operation of the stop operation unit 424 when the stop operation unit 424 and the ratchet operation unit 427 are automatically operated.

In addition, the ratchet module 420 may include a ratchet bevel shaft 425 disposed perpendicular to the pitching shaft 12, and a ratchet bevel gear 426 configured to connect the pitching shaft 12 and the ratchet bevel shaft 425. At this time, the ratchet operation unit 427 rotates the ratchet bevel shaft 425 automatically or manually.

Although not shown, the ratchet module 420 may include: a ratchet bevel shaft disposed perpendicular to the pitching shaft 12, a ratchet bevel gear configured to connect the pitching shaft 12 and the ratchet bevel shaft; a ratchet gear provided on the ratchet bevel shaft and configured to rotate together with the ratchet bevel shaft; a stop member formed longitudinally in a circumferential direction of the ratchet gear and detachably coupled with the ratchet gear; a stop elastic member configured to make the stop member elastically press the ratchet gear; a stop operation unit configured to make the stop member perform a pivot movement automatically or manually; and a ratchet operation unit configured to rotate the ratchet gear automatically or manually.

Here, the ratchet module 420 further includes a ratchet shaft (not shown) that is provided on the ratchet gear and is configured to rotate together with the ratchet gear, and the ratchet operation unit is configured to rotate the ratchet shaft (not shown).

In addition, the ratchet module 420 may further include a ratchet controller configured to control an operation of the ratchet operation unit according to an operation of the stop operation unit when the stop operation unit and the ratchet operation unit are automatically operated.

Figure 6:
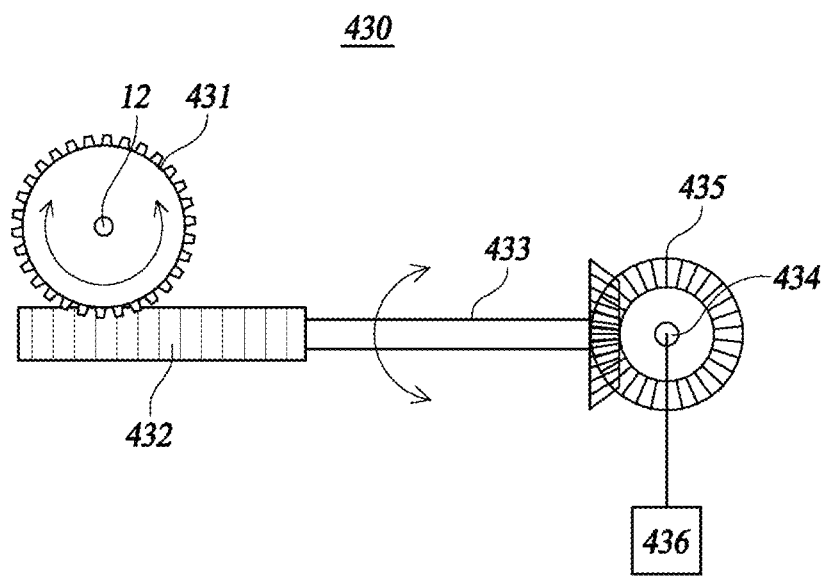
FIG. 6 is a view showing a third example of the pitching coupling unit, which is implemented with a worm gear method, in the bed for the endoscopic examination of the stomach and the large intestine according to the embodiment of the present disclosure.
Figure 7:
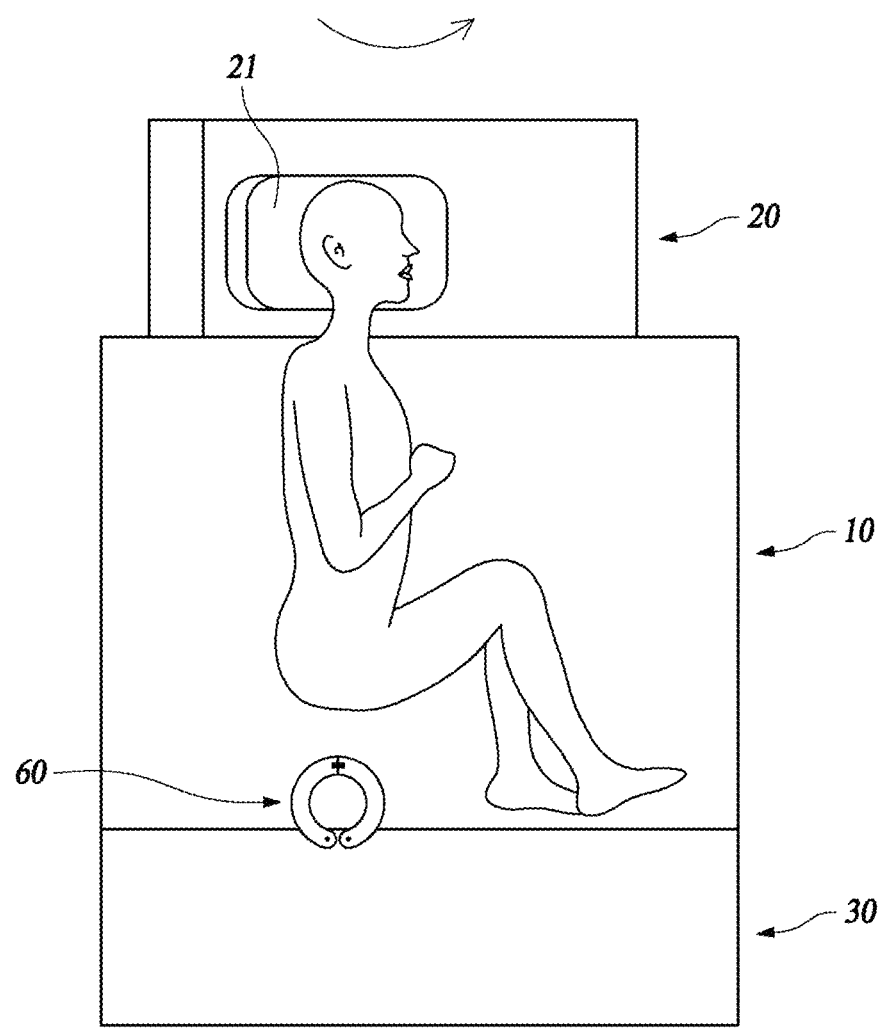
FIG. 7 is a plan view showing a state in which an upper main body is rotated in the bed for the endoscopic examination of the stomach and the large intestine according to the embodiment of the present disclosure.

Third, as shown in FIG. 6, the worm gear module 430 may include: a pitching worm wheel gear 431 provided on the pitching shaft 12 and configured to be rotated together with the pitching shaft 12; a pitching worm screw 432 formed longitudinally in a circumferential direction of the pitching worm wheel gear 431 and configured to be gear-coupled to the pitching worm wheel gear 431; a pitching worm rod 433 provided on the pitching worm screw 432 along a longitudinal direction of the pitching worm screw 432; and a pitching worm operation unit configured to rotate the pitching worm rod 433 automatically or manually.

Here, the worm gear module 430 may further include: a pitching bevel shaft 434 disposed perpendicular to the pitching worm rod 433; and a pitching bevel gear 435 configured to connect the pitching worm rod 433 and the pitching bevel shaft 434.

Although not shown, the worm gear module 430 may include:

a pitching bevel shaft disposed perpendicular to the pitching shaft 12; a pitching bevel gear configured to connect the pitching shaft 12 and the pitching bevel shaft; a pitching worm wheel gear provided on the pitching bevel shaft and configured to be rotated together with the pitching bevel shaft; a pitching worm screw formed longitudinally in a circumferential direction of a pitching worm wheel gear and configured to be gear-coupled to the pitching worm wheel gear; and a pitching worm operation unit configured to rotate the pitching worm screw manually or automatically.

Here, the worm gear module 430 may further include a pitching worm rod provided on the pitching worm screw along a longitudinal direction of the pitching worm screw. At this time, the pitching worm operation unit 436 is configured to rotate the pitching worm rod.

The bed for the endoscopic examination of the stomach and the large intestine according to the embodiment of the present disclosure may further include: an upper main body 20 configured to be coupled to the central main body 10 by a rolling shaft 13 at a head side of the patient so that a rolling movement is possible with the central main body 10 as the reference; and a rolling coupling unit 50 configured to allow the upper main body 20 to perform the rolling movement with the central main body 10 as a reference. At this time, the upper main body 20 may be provided with a headrest 21 on which the patient's head is supported.

Figure 9:
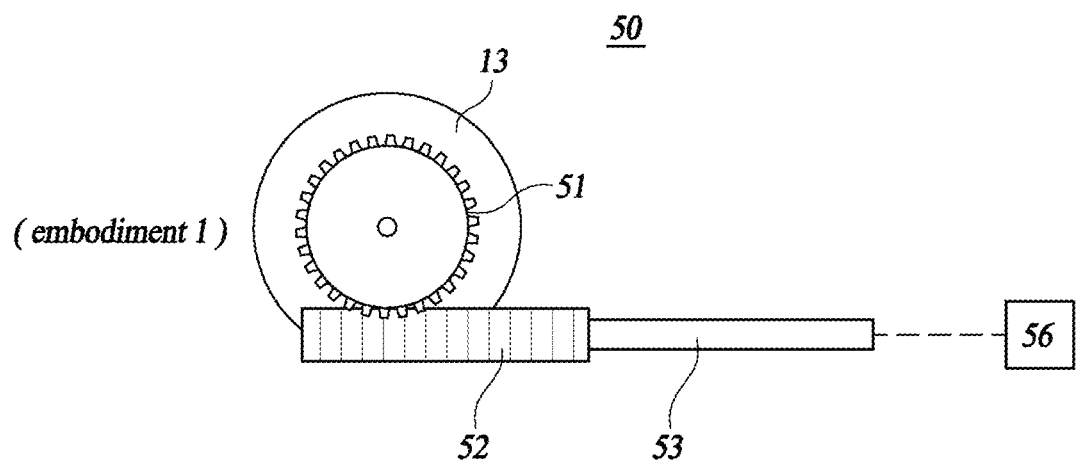
FIG. 9 is a view showing a first example of a rolling coupling unit in the bed for the endoscopic examination of the stomach and the large intestine according to the embodiment of the present disclosure.

As an example, as shown in FIG. 9, the rolling coupling unit 50 may include: a rolling worm wheel gear 51 provided on the rolling shaft 13 and configured to rotate together with the rolling shaft 13; a rolling worm screw 52 formed longitudinally in a circumferential direction of the rolling worm wheel gear 51 and configured to be gear-coupled to the rolling worm wheel gear 51; a rolling worm rod 53 provided on the rolling worm screw 52 along a longitudinal direction of the rolling worm screw 52; and a rolling worm operation unit 56 configured to rotate the rolling worm rod 53 automatically or manually.

At this time, although not shown, the rolling coupling unit 50 may further include: a rolling bevel shaft disposed perpendicular to the rolling worm rod; and a rolling bevel gear configured to connect the rolling worm rod and the rolling bevel shaft to each other.

Figure 10:
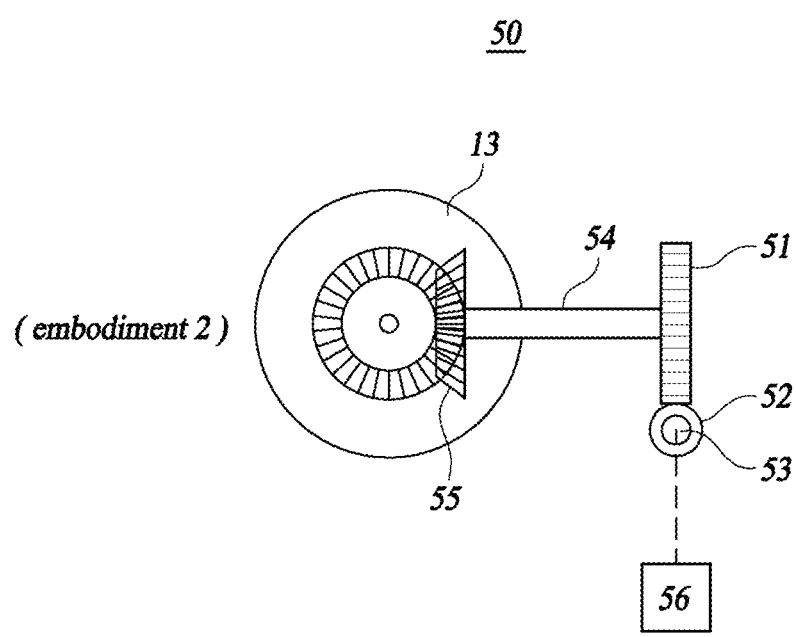
FIG. 10 is a view showing a second example of the rolling coupling unit in the bed for the endoscopic examination of the stomach and the large intestine according to the embodiment of the present disclosure.

As another example, as shown in FIG. 10, the rolling coupling unit 50 may include: a rolling bevel shaft 54 disposed perpendicular to the rolling shaft 13, a rolling bevel gear 55 configured to connect the rolling shaft 13 and the rolling bevel shaft 54 to each other; a rolling worm wheel gear 51 provided on the rolling bevel shaft 54 and configured to be rotated together with the rolling bevel shaft 54; a rolling worm screw 52 formed longitudinally in a circumferential direction of the rolling worm wheel gear 51 and configured to be gear-coupled to the rolling worm wheel girder 51; and a rolling worm operation unit 56 configured to rotate the rolling worm screw 52 manually or automatically.

Here, the rolling coupling unit 50 may further include a rolling worm rod 53 provided on the rolling worm screw 52 along a longitudinal direction of the rolling worm screw 52. Then, the rolling worm operation unit 56 is configured to rotate the rolling worm rod 53.

The bed for the endoscopic examination of the stomach and the large intestine according to the embodiment of the present disclosure may further include a mounting module 60 protrudingly formed in the lower main body 30 and configured to support an endoscopic cable when the lower main body 30 is folded with the central main body 10 as a reference.

The mounting module 60 may include: a mounting part 61 provided in the lower main body 30; a first support ring 62 rotatably coupled to the mounting part 61 with a first shaft 621 as a center; a second support ring 63 rotatably coupled to the mounting part 61 with a second shaft 631 as a center while spaced apart from the first support ring 62; and a locking part 64 configured to couple the first support ring 62 and the second support ring 63 to each other when the first support ring 62 and the second support ring 63 wrap the endoscopic cable.

Here, the mounting part 61 is provided with an accommodating groove part 611 responding to rotations of the first support ring 62 and the second support ring 63, whereby the first support ring 62 and the second support ring 63 may be freely rotated.

In addition, the central main body 10 may be provided with the support groove part 14 recessively formed in order to allow at least the first support ring 62 and the second support ring 63 to be seated therein when the lower main body 30 is substantially horizontal with the central main body 10.

In the embodiment of the present disclosure, the mounting part 61 may be configured to be moved up and down in the lower main body 30 as shown in FIGS. 3A and 3B.

Then, the mounting part 61 may be configured to be detachable from the lower main body 30.

Here, the mounting module 60 may further include: a longitudinal groove 65 recessively formed in the lower main body 30; and a lifting rod 66 extending from the mounting part 61 and configured to be slidingly movable in a state of being fittedly coupled in the longitudinal groove 65.

The mounting module 60 may further include a fixed position part configured to fix the lifting rod 66 to the lower main body 30 at a position where the lifting rod 66 is slidingly moved when the lifting rod 66 is slidingly moved in the longitudinal groove 65.

The fixed position part 67 may include: a plurality of fixed position groove parts 671 recessively formed in a longitudinal direction on an inner surface of the longitudinal groove 65; an elastic seating groove part 672 recessively formed on an outer circumferential surface of the lifting rod 66; an elastic protrusion part 673 configured to be coupled to the elastic seating groove part 672 so as to be slidingly movable; and an elastic member 674 configured to elastically press the elastic protrusion part 673 toward the outside in the elastic seating groove part 672. Then, as the lifting rod 66 slides in the longitudinal groove 65, the elastic protrusion part 673 is fittedly coupled to the fixed position groove part 671 while being moved along the inner surface of the longitudinal groove 65.

Although not shown, the mounting part 61 may be configured to be slidingly movable in the lower main body 30.

Then, the mounting part 61 may be configured to be detachable from the lower main body 30.

Here, the mounting module 60 may further include: a reciprocating guide formed longitudinally in a width direction of the lower main body 30; and a sliding part provided in the mounting part 61 so as to be slidingly movable in a state of being fittedly coupled with the reciprocating guide.

The mounting module 60 may further include a fixed position part configured to fix the mounting part 61 to the lower main body 30 at a position where the mounting part 61 is slidingly moved when the mounting part 61 is slidingly moved in the lower main body 30.

The fixed position part may include: a plurality of fixed position groove parts recessively formed in a longitudinal direction in the lower main body 30; an elastic seating groove part recessively formed in the mounting part; an elastic protrusion part configured to be coupled to the elastic seating groove part so as to be slidingly movable; an elastic member configured to elastically press the elastic protrusion part toward the outside in the elastic seating groove part. Then, as the mounting part 61 slides in the lower main body 30, the elastic protrusion part is fittedly coupled to the fixed position groove part while being moved along a side surface of the lower main body 30.

From now on, an operation of the bed for the endoscopic examination of the stomach and the large intestine according to an embodiment of the present disclosure will be described.

First, when performing an endoscopic examination of the large intestine, the patient may take a posture with his or her legs crouched while lying on his or her side as shown in FIG. 1.

Figure 2:
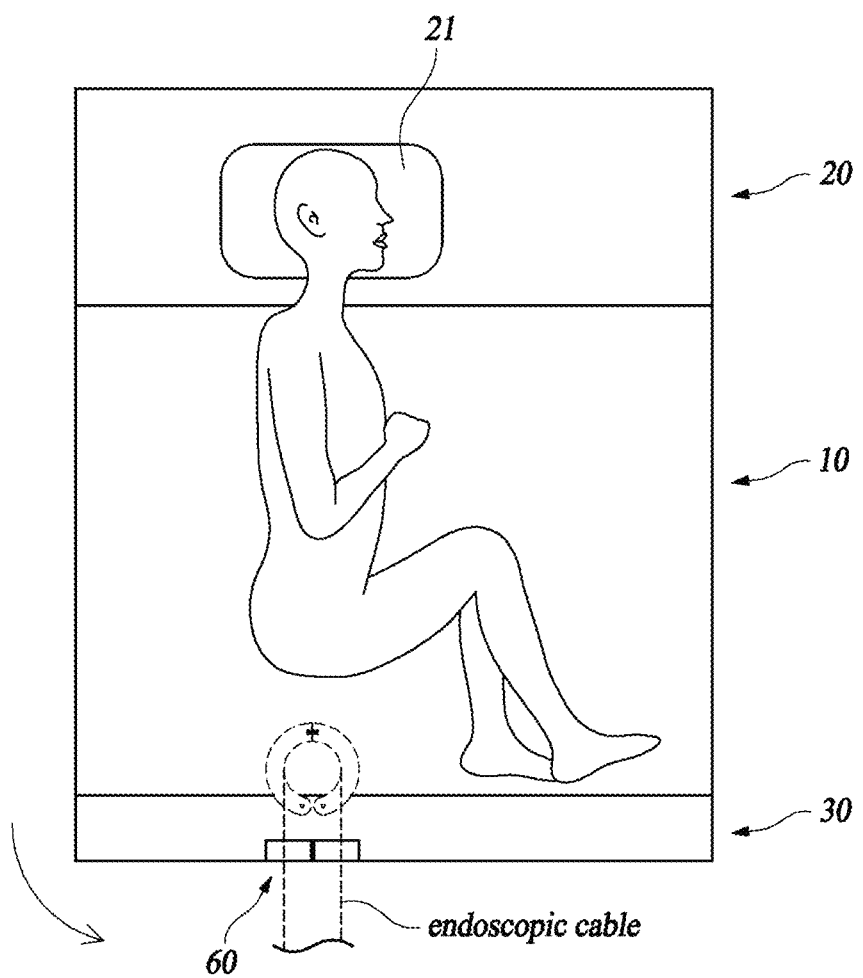
FIG. 2 is a plan view showing a state in which a lower main body is folded in the bed for the endoscopic examination of the stomach and the large intestine according to the embodiment of the present disclosure.

At this time, when the lower main body 30 is forced to perform a pitch movement downward with the central main body 10 as the reference by operating the pitching coupling unit 40, the lower main body 30 is folded from the central main body 10 as shown in FIG. 2 and FIGS. 3A and 3B.

In a process of the endoscopic examination of the large intestine, when a polypectomy or biopsy is to be performed during the endoscopic examination of the large intestine, through a simple operation of coupling the endoscopic cable, the endoscope for the large intestine may be easily fixed to the mounting module 60.

In addition, when the pitching coupling unit 40 is forced to operate to the contrary, the lower main body 30 performs a pitch movement upward with the central main body 10 as the reference.

At this time, when the contrary operation of the pitching coupling unit 40 is stopped, the lower main body 30 may maintain a current position thereof without falling off due to structural characteristics of the pitching coupling unit 40.

Second, when performing endoscopic examination of the stomach, the patient may take a posture with his or her legs crouched while lying on his or her side as shown in FIG. 1.

At this time, when the upper main body 20 is forced to perform a pitch movement to the left or right with the central main body 10 as the reference by operating the rolling coupling unit 50, the upper main body 20 is tilted to the left, for example, from the central main body 10 as shown in FIG.

Figure 8A:
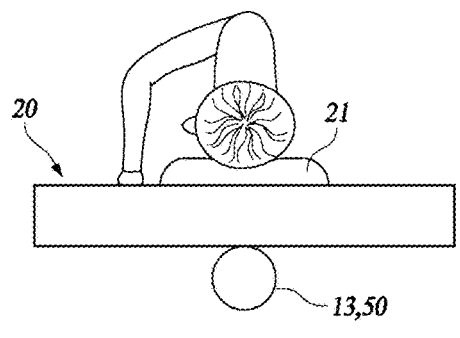
FIGS. 8A and 8B are front views showing operating states of the upper main body in the bed for the endoscopic examination of the stomach and the large intestine according to the embodiment of the present disclosure.
Figure 8B:
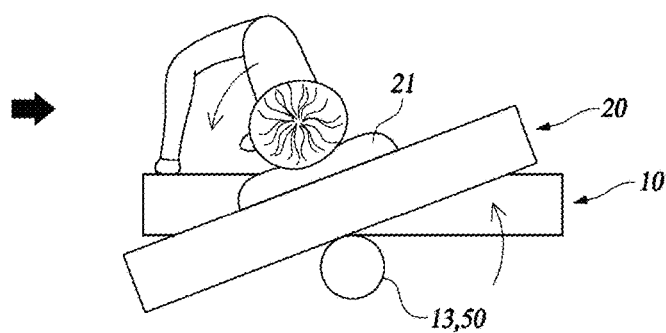

7 and FIGS. 8A and 8B so that a patient's mouth is tilted downward. At this time, when the operation of the rolling coupling unit 50 is stopped, the upper main body 20 may be no longer rotated due to structural characteristics of the rolling coupling unit 50 and may maintain a current position thereof.

At this time, vomiting, or saliva from the mouth naturally flows out during the endoscopic examination process, so the pain of the patient during the endoscopic examination process may be reduced.

In addition, when the rolling coupling unit 50 is operated in an opposite direction, the upper main body 20 may be returned to an initial position.

The bed for the endoscopic examination of the stomach and the large intestine according to another embodiment of the present disclosure may be used for performing the endoscopic examination of the stomach.

The bed for the endoscopic examination of the stomach and the large intestine according to another embodiment of the present disclosure may further include: a central main body 10 configured to support at least a part of the torso and the buttocks of a patient; an upper main body 20 configured to be coupled to the central main body 10 by a rolling shaft 12 at a head side of the patient so that a rolling movement is possible with the central main body 10 as a reference; and a rolling coupling unit 50 configured to allow the upper main body 30 to perform a rolling movement with the central main body 10 as the reference.

The central main body 10, the upper main body 20, and the rolling coupling unit 50 according to another embodiment of the present disclosure have the same configuration as that according to the embodiment of the present disclosure, so a description thereof will be omitted.

According to the bed for the endoscopic examination of the stomach and the large intestine described above, a distance to a patient may be narrowed in a case of the endoscopic examination of the large intestine and a patient's head may be tilted in a case of the endoscopic examination of the stomach.

In addition, it is possible to prevent the lower main body 30 from being rotated downward unexpectedly due to an operation method of the pitching coupling unit 40, so a safety accident may be prevented.

In addition, the lower main body 30 may be supported under a bottom part of the bed by a telescopic mechanism of the pitching coupling unit 40, so it is possible to prevent the lower main body from being rotated downward unexpectedly.

In addition, rotation directions may be limited due to the ratchet gear mechanism in the pitching coupling unit 40, so it is possible to prevent the lower main body 30 from being rotated downward unexpectedly.

In addition, an input part and an output part for rotation may be limited due to the worm gear mechanism in the pitching coupling unit 40, so it is possible to prevent the lower main body 30 from being rotated downward unexpectedly.

In addition, it is possible to prevent the upper main body 20 from an unexpected rolling rotation due to an operation of the rolling coupling unit 40, so a safety accident may be prevented.

In addition, an input part and an output part for rotation can be limited due to the worm gear mechanism in the rolling coupling unit 50, so it is possible to prevent the upper main body 20 from the unexpected rolling rotation to the left and right.

In addition, a bevel gear mechanism may be added, so a position for operating the upper main body 20 may be changed.

In addition, the endoscopic cable may be fixed to a fixed position by using the mounting module 60.

In addition, due to an efficient configuration of the mounting module 60, the endoscopic cable may be gripped using tongs, the state of the endoscopic cable being gripped may be stably maintained, and the detachably-coupled state of the first support ring 62 and the second support ring 63 may be stabilized.

In addition, the height of the mounting part 61 may be efficiently adjusted by using the lifting structure of the mounting module 60.

In addition, the position of the mounting part 61 may be adjusted with a reference of a width direction of the central main body 10 by using the lifting structure of the mounting module 60.

In addition, manpower required for performing the endoscopic examination may be minimized and thus the cost required therefor may be reduced.

Although preferred embodiments of the present disclosure have been described with reference to the drawings as described above, those skilled in the art may modify or alter in various ways the present disclosure without departing from the spirit and scope of the present disclosure as set forth in the claims below.

What is claimed is:

1. A bed for endoscopic examination of the stomach and the large intestine, the bed comprising:
    a central main body configured to support at least a part of the torso and the buttocks of a patient;
    a lower main body configured to be coupled to the central main body by a pitching shaft at a buttocks side of the patient to allow a pitching movement of the lower main body with respect to the central main body;
    a pitching coupling unit configured to allow the lower main body to perform the pitching movement with respect to the central main body; and
    a mounting module protrudingly disposed in the lower main body and configured to support an endoscopic cable when the lower main body is folded with respect to the central main body,
    wherein the mounting module comprises:
        a mounting part provided in the lower main body;
        a first support ring formed in substantially a half-circle, wherein a proximal end of an arc of the first support ring is rotatably coupled to the mounting part;
        a second support ring formed in substantially the half-circle, wherein a proximal end of an arc of the second support ring is rotatably coupled to the mounting part; and
        a locking part configured to couple a distal end of the arc of the first support ring and a distal end of the arc of the second support ring to each other to allow the endoscopic cable to be surrounded between the first support ring and the second support ring.

2. The bed of claim 1, further comprising:
    an upper main body configured to be coupled to the central main body by a rolling shaft at a head side of the patient to allow a rolling movement of the upper main body with respect to the central main body; and
    a rolling coupling unit configured to allow the upper main body to perform the rolling movement with respect to the central main body.

3. The bed of claim 1 or 2, wherein the pitching coupling unit comprises at least any one of:

a sliding module connected at one side thereof to a support leg provided at a part under the central main body and coupled at an opposite side thereof to the lower main body, thereby being configured to adjust a length thereof in a telescopic method;

a ratchet module configured to rotate the pitching shaft forwardly and reversely in a ratchet gear method; and a worm gear module configured to rotate the pitching shaft forwardly and reversely in a worm gear method.

4. The bed of claim 1, wherein the mounting part is configured to be detachable from the lower main body, and wherein the mounting module further comprises:

a longitudinal groove recessively formed in the lower main body; and a lifting rod extending from the mounting part and configured to be slidingly movable in a state of being fittedly coupled in the longitudinal groove.

\* \* \* \* \*